United States Patent [19]
Perrot

[11] 4,351,731
[45] Sep. 28, 1982

[54] PROCESS FOR DIALYZATION OF BLOOD

[75] Inventor: Erwin Perrot, Schwalbach, Fed. Rep. of Germany

[73] Assignee: Klauschenz & Perrot KG, Schwalbach, Fed. Rep. of Germany

[21] Appl. No.: 968,126

[22] Filed: Dec. 11, 1978

Related U.S. Application Data

[62] Division of Ser. No. 838,389, Sep. 30, 1977, Pat. No. 4,137,168.

[30] Foreign Application Priority Data

Oct. 2, 1976 [DE] Fed. Rep. of Germany ....... 2644584

[51] Int. Cl.³ ............................................. B01D 31/00
[52] U.S. Cl. .................................. 210/647; 210/739; 210/96.2
[58] Field of Search ................. 210/22 R, 22 A, 22 B, 210/96 M, 101, 321 A, 321 B, 321 R, 647, 739

[56] References Cited

U.S. PATENT DOCUMENTS

| | | | |
|---|---|---|---|
| 3,352,779 | 11/1967 | Austin et al. | 210/101 X |
| 3,441,136 | 4/1969 | Seafass et al. | 210/96 M |
| 3,939,069 | 2/1976 | Granger et al. | 210/22 A |
| 3,979,284 | 9/1976 | Granger et al. | 210/22 A |
| 4,082,667 | 4/1978 | Seiler, Jr. | 210/96 M |
| 4,083,777 | 4/1978 | Hutchisson | 210/96 M |

Primary Examiner—John Adee

[57] ABSTRACT

Dialysis fluid is produced and transported to a blood dialysis chamber automatically and continuously. A dialysis fluid concentrate and water are mixed and controllably pumped to a buffer storage container from which the mixture is drawn off through the dialysis chamber by a second controllable pump. The second pump is controlled as a function of the quantity of mixture in the buffer container.

10 Claims, 6 Drawing Figures

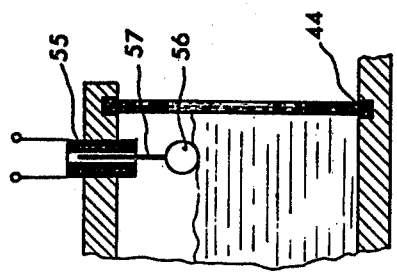
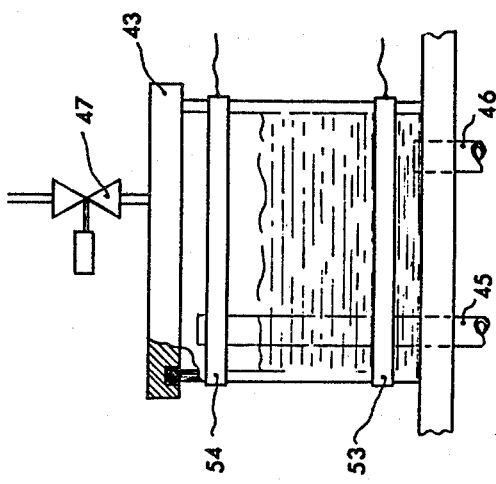
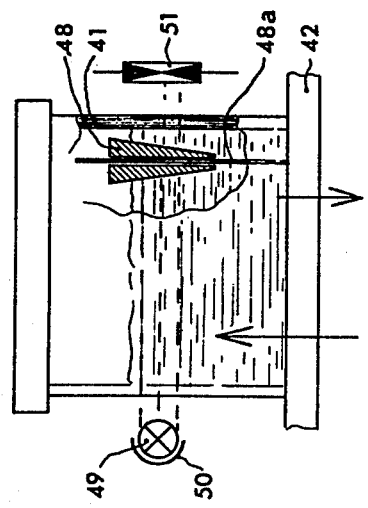
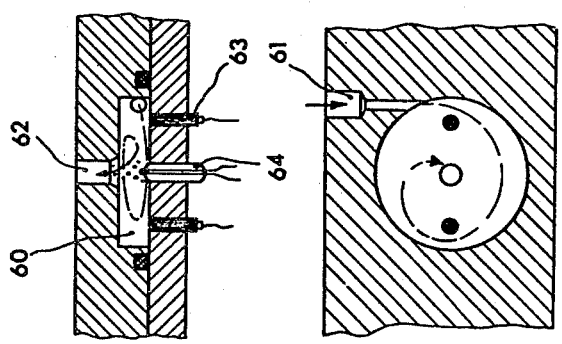

PROCESS FOR DIALYZATION OF BLOOD

CROSS-REFERENCE TO RELATED APPLICATIONS

This application is a division of application Ser. No. 838,389 filed Sept. 30, 1977 and issued as U.S. Pat. No. 4,137,168. Application Ser. No. 838,389 claimed the benefits of the filing date of German Application Ser. No. P 26 44 584 filed Oct. 2, 1976 under the provisions of 35 USC 119 and the International Convention for the protection of industrial property and the same benefits are claimed for the instant application.

BACKGROUND OF THE INVENTION (1) Field of the Invention

The present invention relates to blood dialysis. More specifically, this invention is directed to automatically producing dialysis fluids and transporting such fluids through a dialysis device. Accordingly, the general objects of the present invention are to provide novel and improved methods of such character.

(2) Description of the Prior Art

While not limited thereto, the present invention is especially suited for use with blood dialysis devices such as artificial kidneys. As is known, an artificial kidney includes a vessel which is separated by a semi-permeable membrane into at least a pair of zones through which a dialysis fluid and the blood of the patient respectively flow. The electrolytes and other substances to which the membrane is permeable are exchanged through the membrane during the cleansing or dialysis operation; the exchange occurring in both directions through the membrane. The speed of exchange of the dilutents in the solutions on either side of the dialysis membrane or membranes is largely dependent on the differences of the concentrations of the dilutents on the different sides of the membrane. The passage of water through the dialysis membrane, however, is primarily dependent on the pressure differential thereacross. Thus, the amount of water which passes through the dialysis membrane during a treatment procedure is dependent on the total trans-membrane pressure; this pressure being dependent on the pressure drop between the blood and dialysis fluid flow zones and upon other pressure factors. The pressure dependent passage of water through a dialysis membrane is a phenomenon known in the art as ultra-filtration. The degree of ultra-filtration is a critical factor in the treatment of uremic patients.

It is of extreme importance that the values of the trans-membrane pressure, the concentration of the dialysis fluid and the rate of flow of the dialysis fluid be maintained constant during an entire treatment procedure, which normally takes between six and ten hours, in order to insure that a specific predetermined amount of ultra-filtration and exchange of dilutents will occur. Thus, in order to insure a reliable dialysis, an artificial kidney is provided with a control system for the purpose of regulating the dialysis fluid concentration and temperature. Artificial kidney control systems also include a blood leak detector and various devices which seek to maintain the desired trans-membrane pressure.

Blood dialysis techniques as generally described above are known. Presently available types of dialysis equipment, however, share the common disadvantage that the dialysis fluid flow quantity is variable for a selected trans-membrane pressure. Accordingly, available dialysis equipment is provided with overflow systems and continually over produce the dialysis fluid whereby part of the fluid goes directly into waste drainage via the overflow system. The over production of the dialysis fluid guarantees an adequate supply during the dialysis. Since the overflow is at ambient pressure, drainage into a rinsing pan at normal height is impossible; i.e., it is necessary that the drainage downstream of the dialysis device be positioned lower than the overflow level.

A further disadvantage of presently available dialysis equipment and techniques resides in the requirement of an inlet water pressure which is at least 0.2 to 0.3 atmospheres above ambient pressure. There are many situations, for example during summer months on the upper floors of high rise buildings, where sufficient water pressure may not be available and thus the dialysis equipment will not function.

A still further disadvantage of presently available dialysis equipment is that the dialysis fluids can be produced only through setting a constant water/concentrate ratio.

It is advantageous, in order to guard against a component malfunction, to bypass the dialysis fluid through an internal bypass tube rather than to stop the fluid flow. Some of the available dialysis equipment includes bypass systems. These bypass systems, however, have an inherent defect from a safety viewpoint since, in the case of a defective valve, the dialysis fluid will continue to flow through the device or through the bypass without control.

SUMMARY OF THE INVENTION

The present invention overcomes the above briefly discussed and other deficiencies and disadvantages of the prior art by providing a technique for continuously and automatically producing dialysis fluids and by providing apparatus for use in the practice of this novel technique. The method and apparatus of the present invention is characterized by ease of operation and maximum reliability.

In accordance with a preferred embodiment of the present invention, dialysis fluid production is characterized by supplying water at a pre-determined flow rate into a pan or intermediate storage container; this container hereinafter being referred to as the buffer container. The fluid level in the buffer container is controllable by means of measuring device which provides a control signal for application to a suction pump. In one embodiment of the invention the buffer container includes a capacitive liquid level sensor; this sensor typically comprising metal electrodes wrapped around the container vessel above and below the desired fluid level. In another embodiment, the buffer container is equipped with a photoelectric measuring device which may, for example, comprise a cone shaped float guided on a fixed rod and cooperating with a light emitter and corresponding light detector. As a further alternative, the buffer container may be equipped with an inductive measuring device which can be in the form of a magnetic element mounted on a float and moving relative to a fixed coil. As a still further alternative, the buffer container can be equipped with a resistance measuring device in the form of a potentiometer mounted on a float.

Regardless of the type of sensor employed, the suction pump will be controlled as a function of the level of the fluid in the buffer container in the interest of regulating the fluid flow to thereby insure a constant fluid level in the buffer container. This flow control is especially significant if the equipment is to have the capability of operating with various dialysis fluid pressure differentials which may be selected by means of a pressure pump or a flow control valve. A direct relationship between the setting of the flow control valve and a selected constant pressure differential may be established as a function of flow quantity. Since flow quantity remains constant with varying flow control valve setting, a constant pressure differential is established and the accuracy of the flow quantity control thus becomes an indication of the accuracy of the dialysis fluid pressure differential. The suction pump also provides the requisite preset water quantity in the absence of adequate inlet water pressure.

Also in accordance with the present invention, the buffer container may be provided with a vent valve. The closing of this valve permits the purging of air from the fluid supply tubes upstream of the container and permits the apparatus to be easily and rapidly refilled.

As an alternative, a further controllable pump may be used to purge air from the buffer container rather than reliance upon a vent valve. Use of a further pump improves the purging of air as well as the exercise of automatic control over the pressure differential.

A blood dialysis technique in accordance with the present invention may also be characterized by measuring the flow downstream of the actual dialysis device. The flow measuring device may be of the photoelectric type.

Also in accordance with the invention, conductance measuring devices may be provided both upstream and downstream of the buffer container. These conductance measuring devices may comprise flat cylindrical cavities having tangential inlet ports and centrally disposed overflows. Due to the tangential inlet flow, the fluid in the conductance measuring devices is forced to rotate and, as a result of the centrifugal forces, entrained air is forced to the center of the device and purged directly through the central overflow. The inlet port of the conductance measuring devices is preferably small relative to the flow rate in order to improve the effect of the tangential inlet flow.

BRIEF DESCRIPTION OF THE DRAWING

The present invention may be better understood and its numerous objects and advantages will become apparent to those skilled in the art by reference to the accompanying drawing wherein like reference numerals refer to like elements in the several figures and in which:

FIG. 2 is a side elevation view, partly in section, depicting a buffer container in accordance with a first embodiment of the invention;

FIG. 3 is a side elevation view, partly in section, of a buffer container in accordance with a second embodiment of the invention;

FIG. 4 is a partial side elevation view, partly in section, of a buffer container in accordance with a further embodiment of the invention;

FIG. 5 is a partial cross-sectional view of a conductance measuring device in accordance with the present invention; and FIG. 5a is a cross-sectional top view of the apparatus of FIG. 5.

DESCRIPTION OF THE PREFERRED EMBODIMENTS

Figure 1:
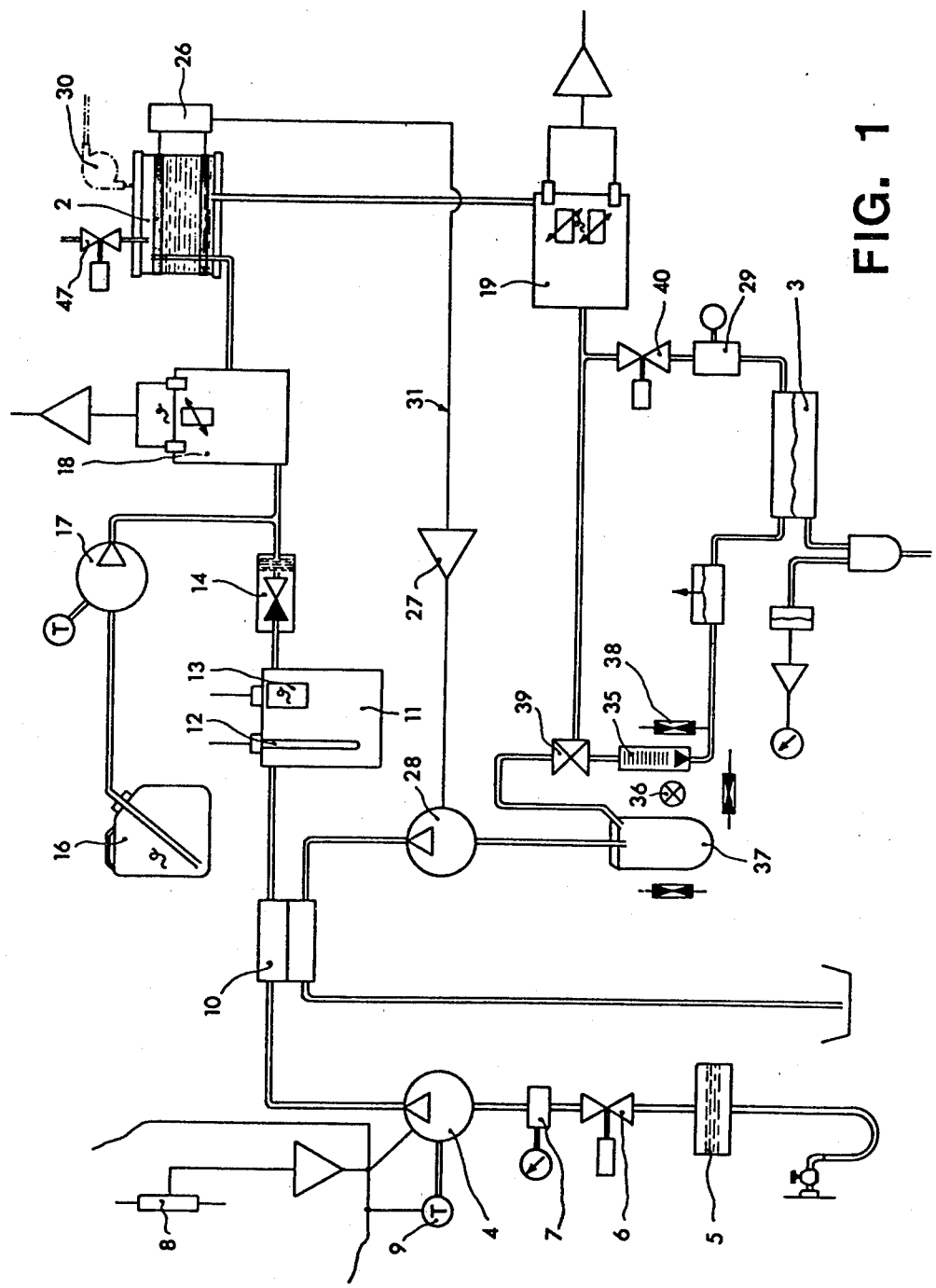
FIG. 1 is a functional block diagram of dialysis equipment for use in practicing the method of a preferred embodiment of the present invention.

With reference to FIG. 1, a dialysis system is shown in the form of a functional block diagram. The actual dialysis device, which includes the exchange membrane, is indicated at 3. The apparatus of FIG. 1 will be connected to a water supply and, in the manner to be described below, a concentrate will be mixed with the received water to produce the dialysis fluid which is delivered to device 3 at a first side of the semi-permeable membrane disposed therein. The dialysis fluid is, prior to delivery to device 3, temporarily stored in a pan or buffer container 2.

The dialysis fluid preparation and transmission subsystem of the apparatus includes a controllable water pump 4. In many cases it is necessary or desirable that the water delivered to the apparatus be preconditioned and, accordingly, a prefilter 5 and a pressure reducing valve 6 may be installed upstream of pump 4. Also, a pressure sensing device, indicated schematically as a manometer 7, may be included between valve 6 and pump 4. The speed of pump 4 will typically be sensed by means of a tachometer 9 and, via a control system including a speed select potentiometer 8, the speed of pump 4 may be controlled in the interest of regulating input water quantity during the dialysis. The use of pump 4 insures that the requisite quantity of water will be furnished to the apparatus even in cases of an abnormally low water supply pressure.

The water which passes through prefilter 5 and pressure reducing valve 6 is pumped through a heat exchanger 10, in order to reclaim heat from the waste dialysis fluid, and is then delivered to a flow-through heater 11. The purpose of heater 11 is to bring the temperature of the water up to 37° C. as required for normal blood dialysis. The flow-through heater 11 includes a heating element 12 and a temperature sensor 13. Warm water outputed from heater 11 will be passed through a venting filter 14 prior to being mixed with the dialysis fluid concentrate.

The dialysis fluid concentrate is stored in a tank 16 and delivered, under the control of a pump 17, to the water line downstream of filter 14. A first conductance measuring device 18, located immediately downstream of the concentrate injection point, controls the dialysis fluid concentration and, as will be obvious from the description of FIGS. 5 and 5a, may also function as a forced mixer for the concentrate and water. Control of the dialysis fluid concentration may, for example, be achieved by exercising control over pump 17 as a function of the output signal of conductance measuring device 18. The conductance measuring device 18 includes a temperature sensor whereby compensation for changes in conductance due to temperature variations in the dialysis fluid may be achieved.

In accordance with the present invention, the apparatus is provided with a second conductance measuring device 19 which is located downstream of the buffer container 2. The second conductance measuring device 19, which is connected in the fluid flow circuit directly ahead of the dialysis device 3, provides for a redundant measurement of the concentration of the dialysis fluid and thus is an important safety feature. The conductance measuring device 19 also includes a temperature sensor which measures the dialysis fluid temperature immediately prior to its delivery to the dialysis device 3.

The dialysis fluid preparation and transport subsystem may be considered as including a supply portion, as described above, and a waste portion; the waste portion being downstream of the buffer container 2. Through measuring the quantity of fluid in container 2, in the manner to be described below, a control signal is generated which is employed to regulate a suction pump 28. The control circuitry for pump 28 includes a signal processing circuit 26 and amplifier 27. Pump 28 is controlled in such a manner as to keep the fluid level in container 2 nearly constant. Thus, if the level of the fluid in container 2 is decreasing, a signal will be provided to pump 28 to vary the speed of the pump to thereby increase the fluid flow until the quantity of fluid in container 2 is replenished to the desired level. Conversely, if the level of fluid in container 2 is increasing, the speed of pump 28 will be varied in the opposite direction.

A pressure reducing valve 29 is installed immediately upstream of dialysis device 3 for the purpose of regulating the fluid flow to device 3. Valve 29 comprises the primary means for controlling the pressure differential across the semi-permeable membrane device 3. Valve 29 is preferably a needle-type valve. For a known valve position and fluid flow rate, a known pressure will be achieved at the outlet of valve 29. Since the rate of flow of dialysis fluid remains constant, by means of the exercise of control of the flow quantity independently of the position of valve 29, a constant pressure differential is created in the dialysis device 3. It is to be noted that the pressure of the dialysis fluid delivered to device 3 may also be controlled by means of a pump 30 connected to buffer container 2 thereby eliminating the need for employing pressure reducing valve 29. In either case, the measurement of the pressure differential is made directly downstream of the dialysis device 3 by means of a contactless electronic measuring device. The effect of the flow control will remain the same regardless of whether valve 29 or pump 30 is employed.

As in the prior art, the present invention contemplates a dialysis fluid bypass as indicated generally at 31. Control over the bypassing of dialysis fluid is achieved by means of a flow meter 35, which includes a lamp 36 of a blood-leak detector 37, and a photosensitive element 38. If the bypass is opened, through operation of the selector valves 39 and 40, no dialysis fluid will flow through the circuit including device 3 if valves 39 and 40 are functioning properly. The flow meter 35 is arranged such that a float disposed therein casts a shadow on the photosensor 38.

Referring jointly to FIGS. 2-4, several alternative arrangements for buffer container 2 and the level sensor associated therewith are shown. Generally, the container or pan consists of a glass vessel 41 having a bottom plate 42 and a cover 43; the bottom plate and cover being hermetically sealted to vessel 41 by means of seals 44. A supply conduit 45 and a withdrawal conduit 46 will pass through bottom plate 42 as shown in FIG. 3. The cover 43 will typically be provided with a vent valve 47.

FIG. 2 depicts a photoelectric system for measuring the level of fluid in container 2. In FIG. 2 a cone-shaped float 48 is mounted on a guide 48a. Float 48 interrupts a light beam which is generated by the combined action of a lamp 49 and mirror 50 and sensed by a photocell 51.

In the embodiment of FIG. 3, a pair of metal rings 53 and 54 extend about glass vessel 41. Rings 53 and 54 are respectively disposed below and above the level at which it is desired to maintain the dialysis fluid in container 2. The sensing of the fluid level is accomplished by means of a capacitance measurement.

In FIG. 4 an inductive measuring scheme is depicted. In the FIG. 4 arrangement in indiction coil 55 is mounted in cover 43 and cooperates with a rod of magnetic material 57 which extends upwardly from a float 56.

Other techniques for measurement of the level of fluid in container 2 may, of course, be utilized. For example, a float coupled to a potentiometer could be employed.

FIGS. 5 and 5a depict in part a conductance measuring-mixing device which may be employed in the practice of the present invention. The conductance measuring device comprises a pair of plates which define a flat cylindrical cavity having a tangential inlet port 61 and a centrally disposed overflow 62. Sensors, typically in the form of carbon electrodes 63, are mounted on the bottom of the cylindrical cavity. A compensation heater 64 is also preferably disposed at the middle of the bottom of the cavity. To improve heat transfer, the heater or heaters 64 will typically extend 1-2 mm, into the cavity. Dialysis fluid delivered to the conductance measuring device will, as a result of the tangential inlet, swirl and entrained air will be pushed toward the middle of the cavity and will be discharged in the form of an air column directly through the central overflow. The measuring electrodes 63 are thus not directly exposed to the air and the accuracy of the conductance measurements in thereby insured. As a result of turbulence resulting from the swirl imparted to the liquid, forced mixing of the dialysis concentrate and water occurs.

While preferred embodiments have been shown and described, various modifications and substitutions may be made thereto without departing from the spirit and scope of the invention. According, it will be understood that the present invention has been described by way of illustration and not limitation.

What is claimed is:

1. In a method for the removal of impurities from a liquid by dialysis, an improved process for controlling the dialysis fluid comprising:

mixing a dialysis fluid concentrate with water to form a dialysis fluid having a preselected concentration;
  delivering a predetermined quantity of the mixed dialysis fluid to a storage container per unit of time;
  withdrawing the dialysis fluid from the storage container and transporting the fluid through a dialysis chamber wherein impurities are transferred to the fluid from the liquid to be purified through a semipermeable membrane;
  constantly measuring the quantity of the dialysis fluid in the storage container; and
  controlling the rate of withdrawal of the dialysis fluid from the storage container in response to the quantity of fluid in the container to maintain a constant quantity in the container.

2. The method of claim 1 wherein the step of mixing comprises:

measuring the concentration of the dialysis fluid prior to delivery to the storage container; and
  varying the quantity of concentrate mixed with the water pursuant to the concentration measurement to achieve the preselected concentration.

3. The method of claim 2 wherein the step of measuring concentration comprises:
measuring the conductance of the dialysis fluid.

4. The method of claim 1 further comprising the step of:
pressuring the stored dialysis fluid.

5. The method of claim 3 further comprising the step of:
pressurizing the stored dialysis fluid.

6. The method of claim 1 further comprising the step of:
heating the water prior to mixing with the dialysis fluid concentrate.

7. The method of claim 6 further comprising the step of:
measuring the concentration of the fluid prior to delivery to the storage container; and
varying the quantity of concentrate mixed with the water pursuant to the concentration measurement to achieve the preselected concentration.

8. The method of claim 7 wherein the step of measuring concentration comprises:
measuring the conductance of the dialysis fluid.

9. The method of claim 7 further comprising the step of:
further measuring the concentration of the dialysis fluid withdrawn from storage.

10. The method of claim 7 further comprising the step of:
pressurizing the container in which the dialysis fluid is stored.

* * * * *